United States Patent [19]
Porter

[11] Patent Number: 5,713,912
[45] Date of Patent: Feb. 3, 1998

[54] LIGATING CLIP HAVING RAMP-SHAPED VESSEL CLAMPING MEMBERS AND TOOL FOR APPLYING SAME

[75] Inventor: Wayne Porter, Bowie, Tex.

[73] Assignee: Stress Management, Inc., Bowie, Tex.

[21] Appl. No.: 650,514

[22] Filed: May 20, 1996

Related U.S. Application Data

[63] Continuation-in-part of Ser. No. 521,233, Aug. 30, 1995.

[51] Int. Cl.⁶ .................................................. A61B 17/08
[52] U.S. Cl. .............................................. 606/158; 606/151
[58] Field of Search ................................ 606/157, 158, 606/151, 120, 207

[56] References Cited

U.S. PATENT DOCUMENTS

| | | |
|---|---|---|
| 3,106,919 | 10/1963 | Churchville . |
| 3,186,047 | 6/1965 | Schwester et al. ................ 24/16 |
| 3,753,438 | 8/1973 | Wood et al. . |
| 3,854,482 | 12/1974 | Laugherty et al. . |
| 3,874,042 | 4/1975 | Eddleman et al. ............... 24/255 |
| 4,291,698 | 9/1981 | Fuchs et al. . |
| 4,346,869 | 8/1982 | MacNeill ............................ 251/10 |
| 4,390,019 | 6/1983 | LeVeen et al. . |
| 4,418,694 | 12/1983 | Beroff et al. . |
| 4,449,531 | 5/1984 | Cerwin et al. . |
| 4,476,865 | 10/1984 | Failla et al. . |
| 4,487,205 | 12/1984 | Di Giovanni et al. . |
| 4,492,232 | 1/1985 | Green . |
| 4,512,345 | 4/1985 | Green . |
| 4,550,729 | 11/1985 | Cerwin et al. . |
| 4,667,671 | 5/1987 | Danzing . |
| 4,807,622 | 2/1989 | Ohkaka et al. . |
| 4,870,965 | 10/1989 | Jahanger . |
| 4,976,722 | 12/1990 | Failla ............................... 606/157 |
| 5,127,915 | 7/1992 | Mattson .......................... 606/120 |
| 5,160,339 | 11/1992 | Chen et al. ..................... 606/158 |

OTHER PUBLICATIONS

Instruction publication for using the Cast–Clip, K–Vet, Inc., 312 N. B Street, Washington, KS 66968, not dated.

*Primary Examiner*—Michael Buiz
*Assistant Examiner*—Patrick W. Rasche
*Attorney, Agent, or Firm*—Dunlap & Codding, P.C.

[57] ABSTRACT

A ligating clip having surfaces with slanted ramp members for clamping a tubular vessel. The ligating clip includes a pair of legs, each of which has a proximal end, a distal end and an inner surface. The proximal ends of the legs are joined to define a hinge. The legs may be forced together onto a tubular vessel such that the inner surfaces of the legs are face-to-face in a closed position. A lock tab protrudes inward from the inner surface near the distal end of one of the legs. A lock slot is provided in the inner surface near the distal end of the other leg. The lock slot receives the lock tab to secure the ligating clip in the closed position. A number of ramp members extend angularly inward from the inner surface of each leg in order to keep the tubular vessel from slipping in the distal direction as the ligating clip is closed. A tool for applying the ligating clip is provided with a cutting blade for severing the vessel after the ligating clip has been applied.

10 Claims, 4 Drawing Sheets

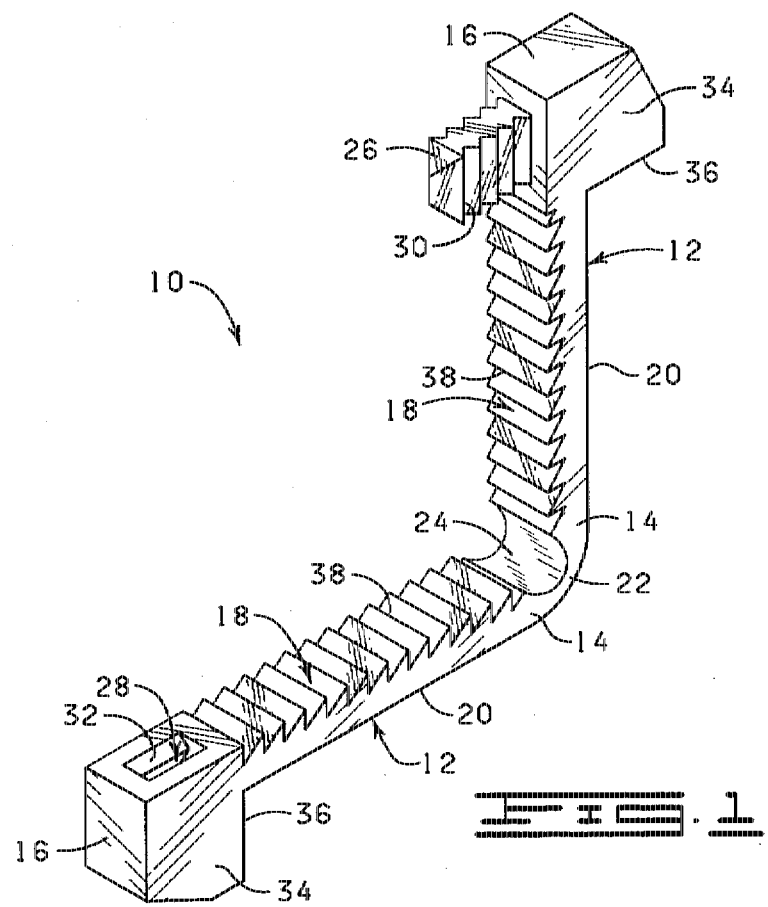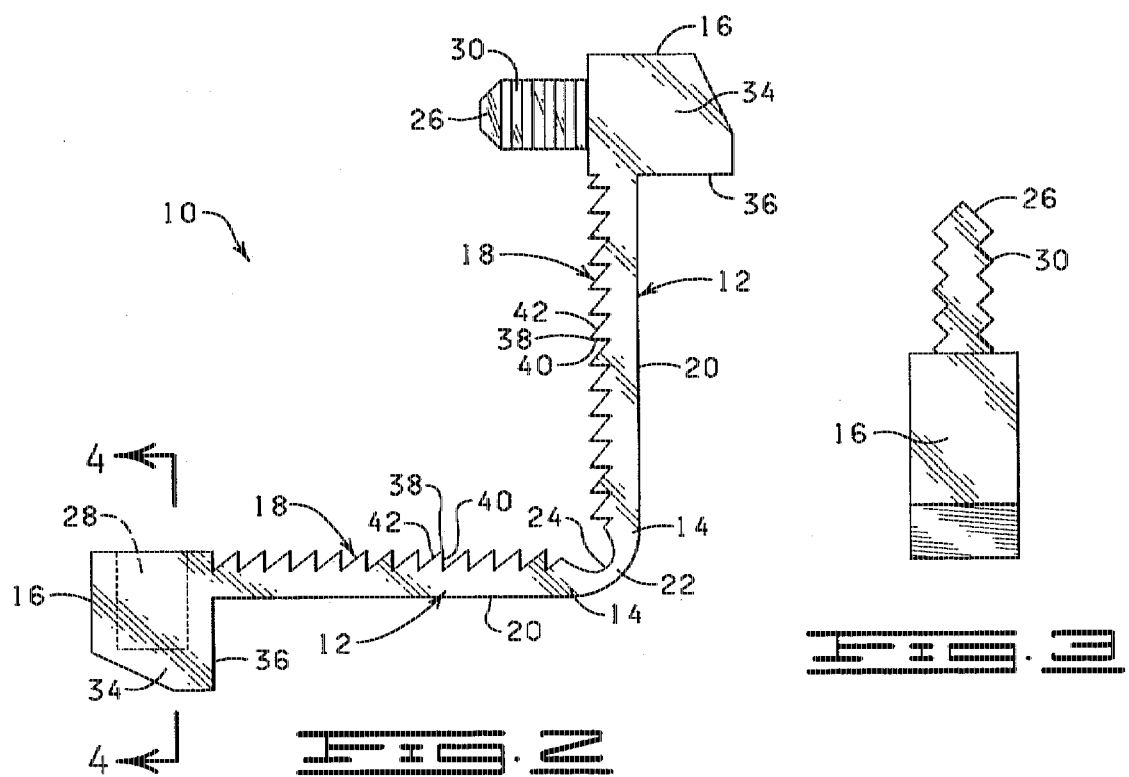

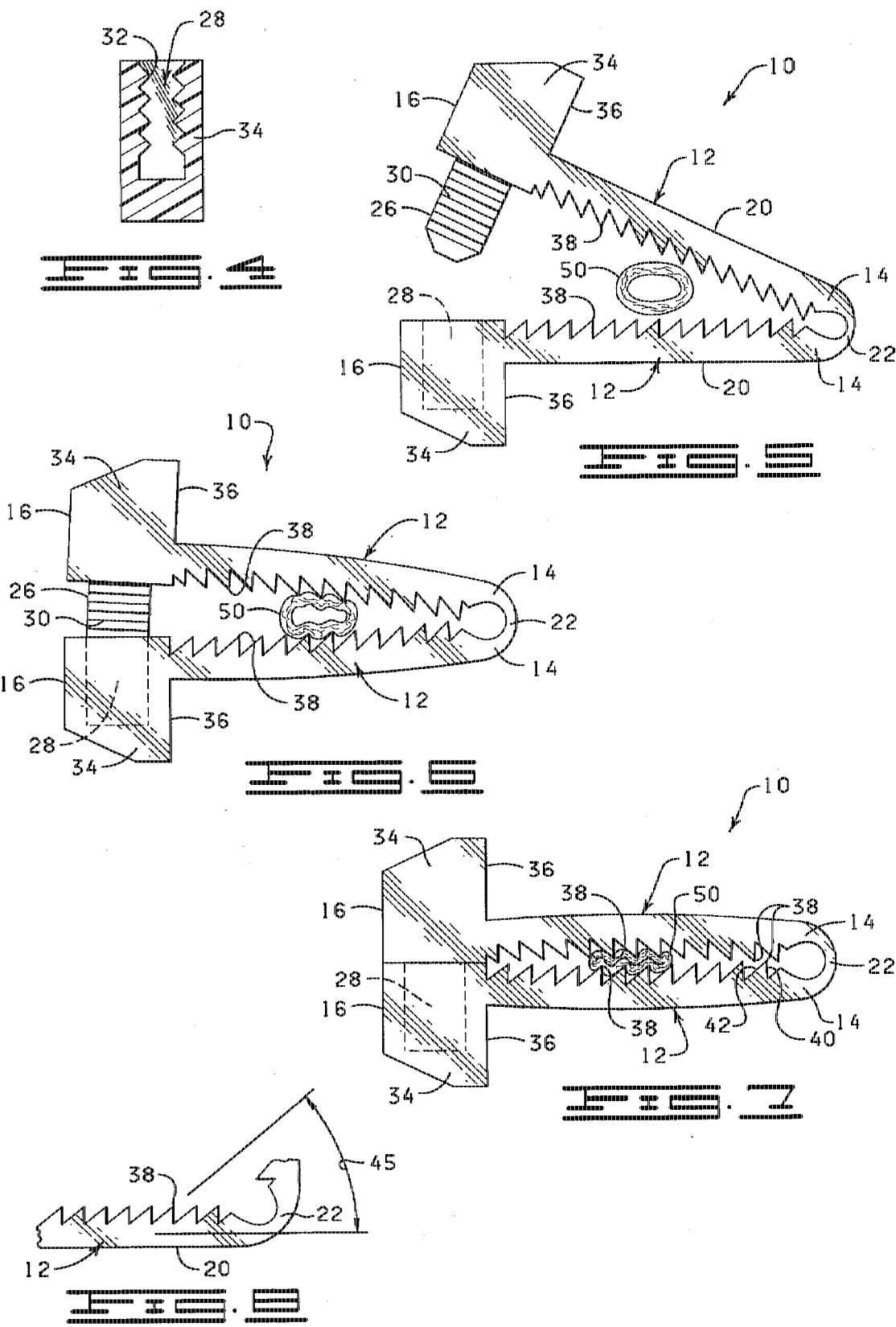

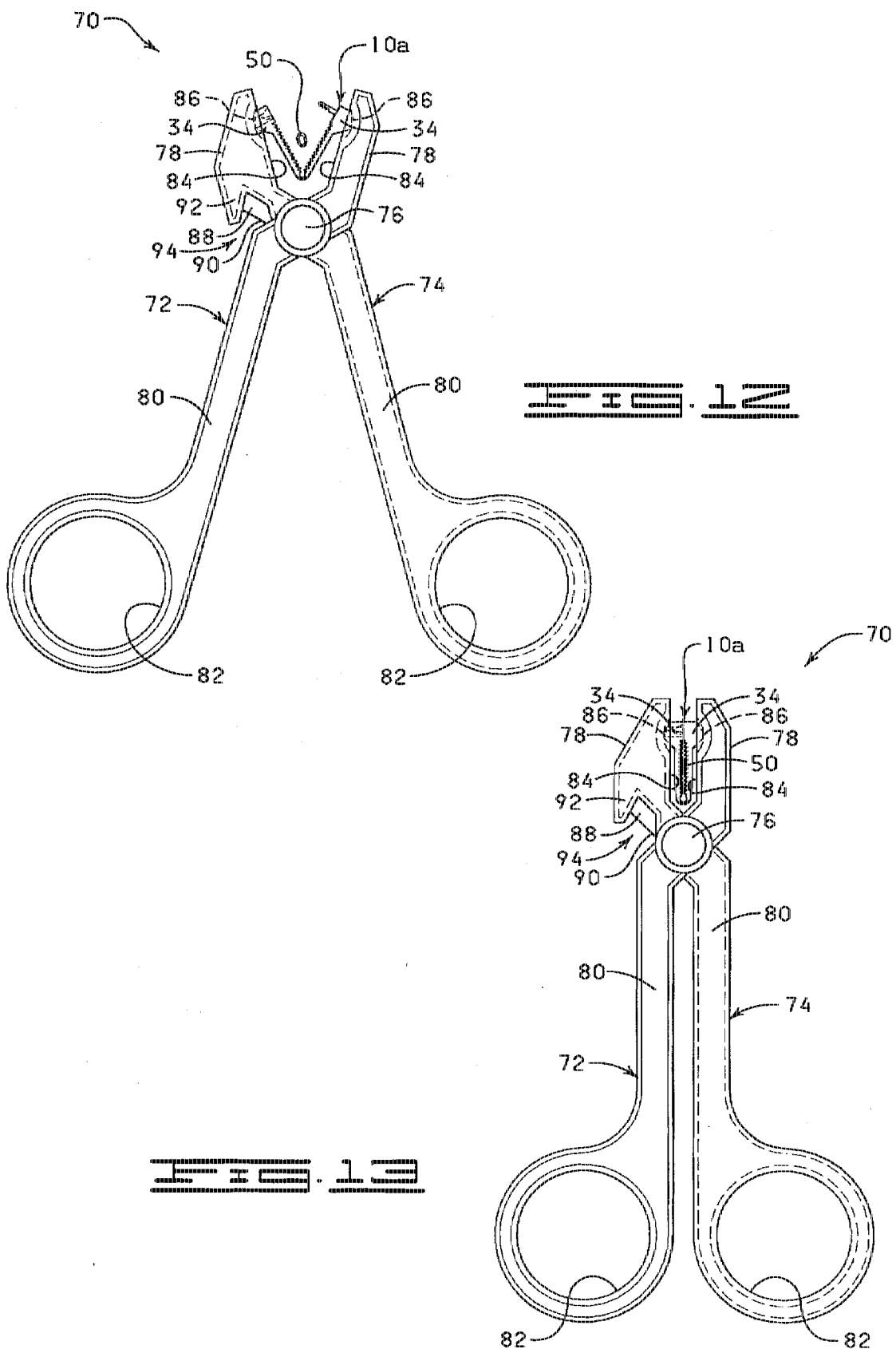

5,713,912

LIGATING CLIP HAVING RAMP-SHAPED VESSEL CLAMPING MEMBERS AND TOOL FOR APPLYING SAME

CROSS-REFERENCE TO RELATED APPLICATIONS

This application is a continuation-in-part of U.S. application Ser. No. 08/521,233, entitled "LIGATING CLIP HAVING RAMP-SHAPED VESSEL-CLAMPING MEMBERS," filed Aug. 30, 1995.

BACKGROUND OF THE INVENTION

1. Field of the Invention

The present invention relates generally to ligating clips, and particularly, but not by way of limitation, to ligating clips for clamping off the vessels of an animal being castrated.

2. Description of Related Art

Various types of ligating clips are known in the art. Most of the conventional clips are surgical or hemostatic clips for use on the vessels of human beings. Such clips have many different designs for the faces which cooperate to close off the vessel.

For example, U.S. Pat. No. 4,449,531 discloses hemostatic clips with flat vessel clamping faces. On the other hand, U.S. Pat. No. 4,346,869 discloses a tube clamp having concave and convex clamping members. U. S. Pat. No. 4,390,019 issued to LeVeen et al. discloses a blood vessel clamp which has a cushion of resilient material on the clamping surfaces.

A clamp for thin-walled tubing is disclosed in U.S. Pat. No. 3,874,042. This particular clamp has at least two spaced longitudinal ridges on one mating member and longitudinal grooves on the second mating member.

U.S. Pat. No. 3,854,482 issued to Laugherty et al. discloses an umbilical cord clamp. This clamp has teeth for gripping a cord on the inner edge portions of its arms. These teeth protrude in a direction which is normal to the arms.

These clips may work well on human subjects, in which case the vessels being ligated can be held securely during application of the clip. However, when used to clamp vessels of animals being castrated, conventional clips are plagued with a common problem: the vessels tend to be pushed out of the clip by the closing action of the clip. This problem is exacerbated by slippery soft tissue and body fluids which accompany the vessels and the task of immobilizing a nervous and impatient animal weighing hundreds of pounds.

SUMMARY OF THE INVENTION

The present invention is a ligating clip which holds the vessel within the clamping surfaces as the clip is closed on the vessel. This "holding in" action compensates for the "pushing out" action caused by the closure of the clip.

A ligating clip constructed in accordance with the present invention includes a pair of legs, wherein each one of the legs has a proximal end, a distal end and a vessel-clamping surface. The proximal ends of the legs are connected to define a hinge.

The distal end of one leg has a lock tab and the distal end of the other leg has a lock slot. When the clip is closed, the lock slot receives the lock tab and secures the clip in the closed position.

The vessel-clamping surfaces of the legs are the surfaces which face one another. Both vessel-clamping surfaces have a plurality of protruding ramp members. Each ramp member is slanted inward toward the hinge of the ligating clip.

One object of the present invention is to provide a ligating clip which is particularly suitable for use in conjunction with the castration of calves and other animals.

Another object of the present invention is to provide a ligating clip which does not have the tendency to push vessels out of the clip as the clip is closed onto the vessels.

Other objects, features and advantages of the present invention are apparent from the following detailed description when read in conjunction with the accompanying drawings and appended claims.

BRIEF DESCRIPTION OF THE DRAWINGS

FIG. 1 is a perspective view of a ligating clip constructed in accordance with the present invention.

FIG. 2 is a side view of the ligating clip of FIG. 1.

FIG. 3 is an end view of the ligating clip leg having the lock tab.

FIG. 4 is a sectional view of the ligating clip taken along the lines 4—4 of FIG. 2.

FIG. 5 is a side view of an open ligating clip with a vessel disposed between the vessel-clamping surfaces of the clip.

FIG. 6 is the same view as FIG. 5, but with the clip partially closed on the vessel.

FIG. 7 is the same view as FIG. 6, but with the clip completely closed and locked onto the vessel.

FIG. 8 is a partly diagrammatical view of a portion of one of the legs to illustrate the angular orientation of the ramp members of the ligating clip.

FIG. 12 is a side view of a tool constructed in accordance with the present invention for applying the ligating clip to a vessel. The tool is holding an open ligating clip with a vessel disposed between the vessel-clamping surfaces of the clip.

FIG. 13 is the same view as FIG. 12, but with the tool closed to apply the ligating clip to the vessel.

DETAILED DESCRIPTION OF THE PREFERRED EMBODIMENTS

Figure 9:
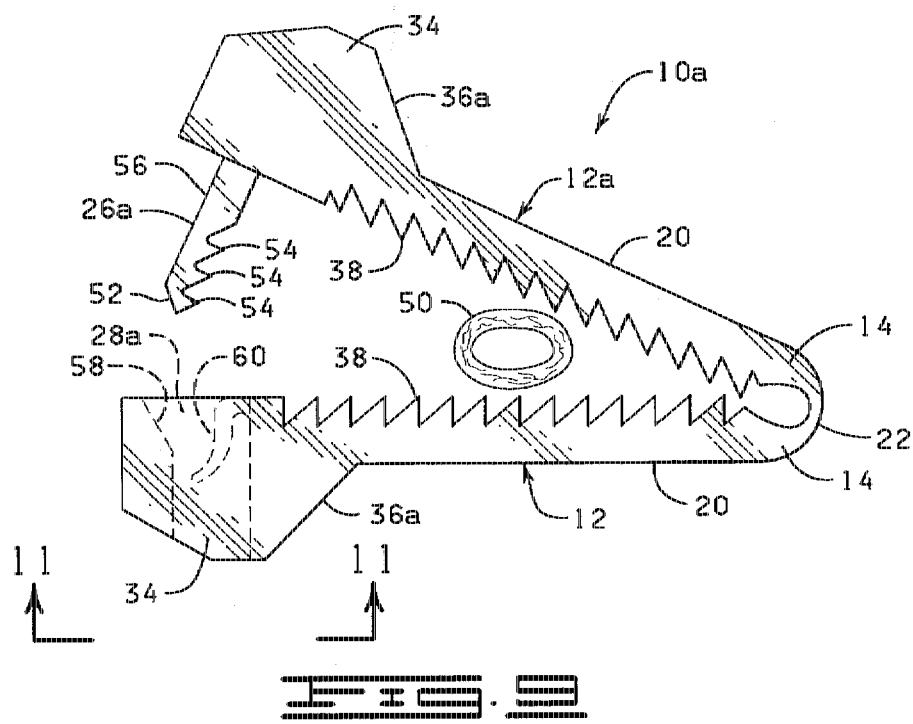
FIG. 9 is side view of an alternate embodiment of a ligating clip constructed in accordance with the present invention. The ligating clip is open with a vessel disposed between the vessel-clamping surfaces of the clip.

Referring to the drawings in general, and to FIGS. 1 and 2 in particular, shown therein and designated by the general reference numeral 10 is a ligating clip constructed in accordance with the present invention. The ligating clip 10 includes a pair of legs 12, wherein each one of the legs 12 has a proximal end 14, a distal end 16, an inner surface 18 and an outer surface 20.

The proximal ends 14 of the legs 12 are joined to define a hinge 22. The legs 12 are movable about the hinge 22 between an open position (FIGS. 1, 2 and 5) and a closed position (FIG. 7). A recessed area 24 is provided at the hinge 22 to facilitate the closing of the ligating clip 10.

A lock tab 26 extends inward from the inner surface 18 of one of the legs 12 near the distal end 16 of the leg 12. Near the distal end 16 of the inner surface 18 of the other leg 12, a lock slot 28 is provided for receiving the lock tab 26 when the ligating clip 10 is closed.

The lock tab 26 and lock slot 28 have a plurality of complementary ridges which cooperate to secure the lock tab 26 within the lock slot 28 when the ligating clip 10 is closed. One of the ridges of the lock tab 26 is designated by reference numeral 30 and is generally representative of the ridges on the lock tab 26 (FIGS. 1 and 3). One of the ridges of the lock slot 28 is designated by reference numeral 32 and is generally representative of the ridges on the lock slot 28.

In a preferred embodiment, the ridges 30 are located on opposite sides of the lock tab 26 and the ridges 32 are positioned on opposite sides of the lock slot 28. The other sides of the lock tab 26 and lock slot 28 are substantially flat surfaces. However, a wide variety of locking mechanisms may be employed to secure the ligating clip 10 in the closed position.

It is desirable that an end portion of the lock tab 26 be tapered. With the tapered end, the lock tab 26 guides itself into the lock slot 28 as the ligating clip 10 is closed.

An ear 34 extends outward at the distal end 16 of each leg 12 of the ligating clip 10. Each ear 34 includes a shoulder 36 which generally faces toward the hinge 22 of the ligating clip 10. The shoulders 36 should be shaped such that the mechanism of any suitable ligating tool may push against the shoulders 36 to force closure of the ligating clip 10.

As illustrated by FIGS. 1 and 2, a plurality of ramp members extend inwardly from the inner surface 18 of each leg 12. One of the ramp members for each leg 12 is designated by reference numeral 38 and is generally representative of the ramp members of the ligating clip 10.

Each ramp member 38 has a hinge-facing surface 40 and a ramp surface 42. Typically, the hinge-facing surface 40 of each ramp member 38 is substantially perpendicular to the lengthwise direction of the leg 12 from which the ramp member protrudes. However, it should be appreciated that the hinge-facing surface 40 of each ramp member 38 may slant to define either an acute or an obtuse angle with respect to the lengthwise line of the respective leg 12.

On the other hand, the ramp surface 42 of each ramp member 38 is slanted angularly inward from the lengthwise direction of the leg 12 from which the ramp member protrudes. Thus, the ramp members 38 protrude angularly inward from the inner surface 18 of the respective leg 12 such that each ramp member 38 and the portion of the respective leg 12 extending toward the hinge 22 define an acute angle. As illustrated by FIG. 8, this acute angle 45 is typically between about 30 degrees and 60 degrees and is preferably an angle of approximately 45 degrees.

Each ramp member 38 has a base and tapers to an innermost edge. Thus, the ramp members 38 resemble a saw-toothed arrangement when viewed from the side, as illustrated by FIG. 2.

As best shown in FIG. 1, each ramp member 38 typically extends transversely all the way across the respective leg 12 of the ligating clip 10. However, it should be appreciated that each ramp member 38 may extend across only a part of the respective leg 12.

The ligating clip 10 may be constructed in a wide variety of sizes. It should be appreciated that different sizes of clips may be required for optimal use on different sizes and types of animals. However, for a typical calf, a suitable ligating clip 10 has legs 12 which are about 21 millimeters in length and 2.5 millimeters in width. A leg 12 with these dimensions typically has 8 to 16 ramp members 38 which are from 0.5 to 1.0 millimeters in length.

The ligating clip 10 may be constructed of any suitable metallic or nonmetallic material which is known in the art. Further, the ligating clip 10 may be made of an absorbable or a non-absorbable substance.

For non-absorbable materials, the ligating clip 10 may be made of nylon, polypropylene or the like. For making a clip which is absorbable, the ligating clip 10 may be constructed of homopolymers and copolymers of glycolide and lactide, p-diaxanone or any other absorbable polymers known in the art.

Operation

The application of the ligating clip 10 to a vessel is best understood with reference to FIGS. 5 through 7. As shown in FIG. 5, the open ligating clip 10 is positioned with the legs 12 on opposing sides of a tubular structure or tubular vessel 50. The longitudinal axis of the vessel 50 and the legs 12 of the ligating clip 10 are generally perpendicular to one another. The tubular vessel 50 is situated in an intermediate area between the ramp members 38 of the two legs 12.

In FIG. 5, the ligating clip 10 is partially closed on the tubular vessel 50. As the ligating clip 10 is closed, the angular orientation of the ramp members 38 applies a gripping force toward the hinge 22 on the vessel 50 and offsets the tendency of the vessel 50, made slippery by soft tissue and body fluids, to slide toward the distal ends 16 of the legs 12. At approximately this point, the lock tab 26 begins to enter the lock slot 28 and the ridges 30 and 32 of the lock tab 26 and lock slot 28, respectively, begin to interlock.

As illustrated by FIG. 7, the ligating clip 10 finally is closed completely on the tubular vessel 50 to constrict flow through the vessel 50. The ridges 30 and 32 of the lock tab 26 and the lock slot 28 are fully interlocked to secure the ligating clip 10 on the vessel 50.

It should be appreciated that upon closure of the ligating clip 10 the ramp members 38 of one leg 12 are offset from the ramp members 38 of the opposing leg 12. Thus, when the ligating clip 10 is closed, each ramp member 38 of one leg 12 is proximate to, or engages, the ramp surface 42 of one of the ramp members 38 of the opposing leg 12 (See FIG. 7).

Figure 10:
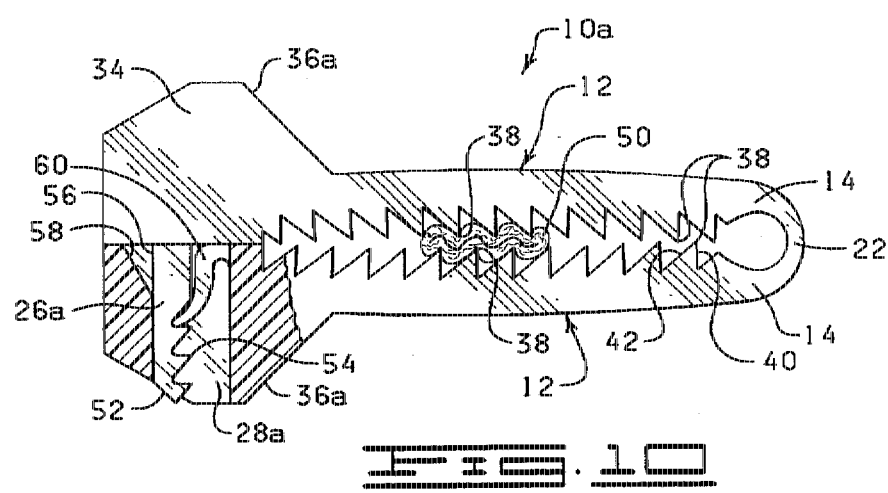
FIG. 10 is the same view as FIG. 9, but with the ligating clip closed on the vessel. For purposes of illustration, the latching portion of the ligating clip is shown in cross-section.
Figure 11:
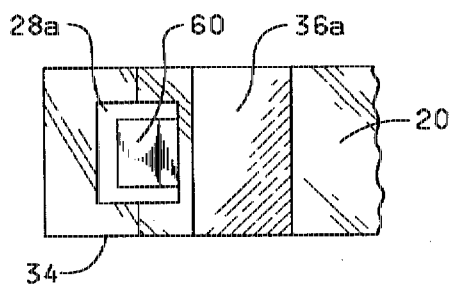
FIG. 11 is a view of the portion of the ligating clip indicated by lines 11—11 in FIG. 9.

Embodiment of FIGS. 9 through 11

With reference to FIGS. 9 through 11, shown therein and designated by reference character 10a is an alternate embodiment of a ligating clip constructed in accordance with the present invention. The ligating clip 10a is substantially the same as the ligating clip 10 except for the latching mechanism.

As shown in FIGS. 9 and 10, the ligating clip 10a has a modified lock tab 26a, lock slot 28a and shoulders 36a. The lock tab 26a has a beveled end 52 for guiding the lock tab 26a into the lock slot 28a.

Further, the lock tab 26a has a plurality of ramp members 54 on the face of the lock tab 26a facing the hinge 22. The ramp members 54 of the lock tab 26a point angularly away from the beveled end 52. The side 56 of the lock tab 26a facing away from the hinge 22 is substantially flat to facilitate entry of the lock tab 26a into the lock slot 28a.

The lock slot 28a extends all the way through the ear 34 and has outwardly sloping wall 58 which provides an enlarged entry area for the lock tab 26a. When the clip 10a is closed, the beveled end 52 may strike the sloping wall 58 and be guided on into the lock slot 28a. This construction facilitates the closure of the ligating clip 10a.

Just within the lock slot 28a opposite the sloping wall 58, a lock tongue 60 is provided. The lock tongue 60 may be molded with the entire ligating clip 10a as one piece. Thus, the lock tongue 60 may be made of the same material as the rest of the ligating clip 10a.

As best seen in FIG. 10, the lock tongue 60 should be flexible enough to allow the lock tab 26a to be inserted into the lock slot 28a. However, the lock tongue 60 should be rigid enough to remain engaged against one of the ramp members 54 to secure lock the lock tab 26a in the lock slot 28a.

It should be appreciated that upon closure of the ligating clip 10a the ramp members 38 of one leg 12 are offset from the ramp members 38 of the opposing leg 12. Thus, when the ligating clip 10a is closed, each ramp member 38 of one leg 12 is proximate to, or engages, the ramp surface 42 of one of the ramp members 38 of the opposing leg 12 (See FIG. 11).

Tool for Applying Ligating Clips

With reference to FIGS. 12 and 13, shown therein and designated by reference numeral 70 is a tool for applying ligating clips 10a to a vessel 50. The tool 70 includes a pair of clamping members 72 and 74 joined by a pivot pin 76 for scissors-like movement.

Each one of the clamping members 72 and 74 comprises a jaw 78 at the forward end, an elongated handle 80 and a thumb or finger loop 82 at the rearward end. By operating the finger loops 82 with the thumb and finger, the tool 70 may be opened (FIG. 12) or closed (FIG. 13) in same manner as a pair of scissors.

The jaws 78 have facing surfaces 84 with recesses 86 shaped to receive the ears 34 of the ligating clip 10a. In this manner, the ears 34 of a ligating clip 10a may be disposed in the recesses 86 of the jaws 78 and the open ligating clip 10a may be carried by the tool 70 to position the vessel-clamping surfaces of the ligating clip 10a on opposing sides of the vessel 50 (FIG. 12). Then the finger loops 82 are moved together to clamp the ligating clip 10a onto the vessel 50 (FIG. 13).

Once the ligating clip 10a is clamped onto the vessel 50, the vessel 50 may be severed at a fluid flow point past the ligating clip 10a. Severing the vessel 50 may be done with a separate instrument. However, laying down the tool 70 and picking up a knife is awkward and increases the chance of an accidental cut.

In order to obviate the need for a separate knife, the tool 70 is provided with its own blade 88. The blade 88 has a cutting edge 90 which extends from the outer side of one clamping member 74 near the pivot pin 76 and faces angularly back toward the finger loop 82 of the other clamping member 72.

The jaw 78 of clamping member 74 has a hook extension 92 which protrudes toward the finger loop 82 of clamping member 72 to function as a blade guard against unnecessary exposure of the sharp cutting edge 90. The hook extension 92 of clamping member 74 and the handle 80 of clamping member 72 define a guideway 94 for the vessel 50 into severing contact with the cutting edge 90 of the blade 88.

It should be appreciated that the tool 70 may have blades 88 on either one of clamping members 72 and 74 or on both clamping members. Further, the tool 70 may be used for ligating and severing whether the tool 70 is turned such that the blade 88 is toward the right-hand or left-hand side of the tool 70.

In operation, the tool 70 is used to clamp a ligating clip 10a onto the vessel 50 as described hereinabove. Next, the tool 70 is opened to free the jaws 78 of the tool 70 from the ligating clip 10a.

Then, while holding the vessel 50 with one hand, the tool 70 is drawn across the vessel 50 such that the vessel 50 enters the guideway 94 and is severed by the cutting edge 90 of the blade 88. Typically, the tool 70 is closed during the severing operation to have increased leverage and make it easier to dispose the vessel 50 into the guideway 94. The closed position is illustrated by FIG. 13, except that a ligating clip 10a would not be disposed in the jaws 78 during the vessel-severing operation.

Changes may be made in the combinations, operations and arrangements of the various parts and elements described herein without departing from the spirit and scope of the invention as defined in the following claims.

What is claimed is:

1. A ligating clip comprising:

a first leg and a second leg, each one of the legs having a proximal end, a distal end and a vessel-clamping surface between the proximal and distal ends thereof, the proximal ends of the legs being joined with the vessel-clamping surfaces of the legs disposed toward one another to define a hinge such that the clip may be disposed in an open position wherein the vessel-clamping surfaces of the legs are spaced apart and a closed position wherein the vessel-clamping surfaces are substantially together facing one another, the first leg having a lock slot extending into a distal area thereof, the lock slot being located to face a distal area of second leg when the first and second legs are moved to the closed position;

a lock tab extending from a distal area of the second leg, the lock tab being located such that the lock tab enters into the lock slot of the first leg when the first and second legs are moved into the closed position, the lock tab having a plurality of lock members protruding therefrom;

a lock tongue extending from one of the interior walls of the lock slot into the lock slot, the lock tongue being located to engage at least one of the lock members of the lock tab when the lock tab is disposed within the lock slot and thereby lock the first and second legs into the closed position and a plurality of ramp members protruding from the vessel-clamping surface of each one of the legs, wherein each one of the ramp members extends angularly toward the opposing leg at a slant toward the hinge.

2. The ligating clip of claim 1 wherein the lock tab has a beveled end.

3. The ligating clip of claim 1 wherein the first leg has a sloping wall at the entry to the lock slot, the sloping wall being positioned and angled to engage the lock tab and guide the lock tab into the lock slot as the first and second legs are moved into the closed position.

4. The ligating clip of claim 1 wherein the lock tab has a beveled end and the first leg has a sloping wall at the entry to the lock slot, the sloping wall being positioned and angled such that the sloping wall and the beveled end of the lock tab cooperate to guide the lock tab into the lock slot as the first and second legs are moved into the closed position.

5. The ligating clip of claim 1 wherein the ramp members define a saw-toothed arrangement.

6. The ligating clip of claim 1 wherein each one of the ramp members extends substantially across the entire vessel-clamping surface of the corresponding leg.

7. The ligating clip of claim 1 wherein each one of the ramp members has a surface facing the hinge.

8. The ligating clip of claim 1 wherein the ramp surface of each one of the ramp members extends at an angle between about 30 and 60 degrees with the lengthwise direction of the leg from which the ramp member protrudes.

9. The ligating clip of claim 1 wherein the ligating clip is constructed of an absorbable polymer.

10. The ligating clip of claim 1 wherein the ligating clip is constructed of a substance selected from the group consisting of nylon, polypropylene, lactide homopolymer, lactide copolymer, glycolide homopolymer, glycolide copolymer and p-diaxanone.

* * * * *